US 7,959,579 B2

(12) United States Patent
Dijkman (10) Patent No.: US 7,959,579 B2
(45) Date of Patent: Jun. 14, 2011

(54) APPARATUS FOR MEDICAL MEASUREMENT (75) Inventor: Gerrat Dijkman, Enschede (NL)

(73) Assignee: Laborie Medical Technologies, Inc., Mississauga, Ontario (CA)

( * ) Notice: Subject to any disclaimer, the term of this patent is extended or adjusted under 35 U.S.C. 154(b) by 936 days.

(21) Appl. No.: 11/624,177

(22) Filed: Jan. 17, 2007

(65) Prior Publication Data

US 2007/0179400 A1 Aug. 2, 2007

Related U.S. Application Data (63) Continuation of application No. 10/572,031, filed as application No. PCT/NL03/00635 on Sep. 12, 2003, and a continuation-in-part of application No. 10/521,340, filed as application No. PCT/NL03/00508 on Jul. 10, 2003, now abandoned.

(30) Foreign Application Priority Data

Jul. 12, 2002 (NL) ...................................... 1021054

(51) Int. Cl.
*A61B 5/00* (2006.01)
*A61B 5/02* (2006.01)
*A61B 5/117* (2006.01)
*A61B 8/14* (2006.01)
(52) U.S. Cl. ......... 600/561; 600/468; 600/488; 600/587
(58) Field of Classification Search .................. 600/561, 600/486, 488, 587
See application file for complete search history.

(56) References Cited

U.S. PATENT DOCUMENTS

| 4,576,181 | A | * | 3/1986 | Wallace et al. | 600/488 |
|---|---|---|---|---|---|
| 4,589,287 | A | * | 5/1986 | Dickens | 73/727 |
| 4,610,256 | A | * | 9/1986 | Wallace | 600/488 |
| 4,642,785 | A | * | 2/1987 | Packard et al. | 702/131 |
| 4,658,829 | A | * | 4/1987 | Wallace | 600/488 |
| 4,679,567 | A | * | 7/1987 | Hanlon et al. | 600/488 |
| 4,762,120 | A | * | 8/1988 | Hussein | 600/136 |
| 4,767,405 | A | * | 8/1988 | Lokken | 604/506 |
| 4,776,343 | A | * | 10/1988 | Hubbard et al. | 600/488 |
| 5,249,576 | A | * | 10/1993 | Goldberger et al. | 600/323 |
| 5,273,047 | A | * | 12/1993 | Tripp et al. | 600/488 |
| 5,305,381 | A | * | 4/1994 | Wang et al. | 379/455 |
| 5,307,263 | A | * | 4/1994 | Brown | 600/301 |
| 5,335,551 | A | * | 8/1994 | Ohnishi et al. | 73/731 |
| 5,425,375 | A | * | 6/1995 | Chin et al. | 600/549 |

(Continued)

FOREIGN PATENT DOCUMENTS

DE 19851275 C1 10/2000

(Continued)

OTHER PUBLICATIONS

Motorola, Inc., "Motorola Semiconductor Technical Data High Volume Pressure Sensor For Disposable Applications," 2002.

*Primary Examiner* — Max Hindenburg
*Assistant Examiner* — Sean P Dougherty
(74) *Attorney, Agent, or Firm* — Cahn & Samuels, LLP (57) ABSTRACT

A measuring device for medical applications in at least one example embodiment includes a first part provided with measuring means for measuring data of a patient, and a second part provided with communication means for sending the data. In at least one example embodiment, the second part is releasably connected to the first part.

21 Claims, 7 Drawing Sheets

U.S. PATENT DOCUMENTS

| | | | |
|---|---|---|---|
| 5,479,934 A | | 1/1996 | Imran |
| 5,522,266 A * | | 6/1996 | Nicholson et al. ............... 73/708 |
| 5,551,300 A * | | 9/1996 | Vurek et al. ..................... 73/706 |
| 5,575,563 A * | | 11/1996 | Chiu et al. ..................... 374/141 |
| 5,609,561 A * | | 3/1997 | Uehara et al. ................. 600/112 |
| 5,617,857 A * | | 4/1997 | Chader et al. ................. 600/424 |
| 5,711,302 A * | | 1/1998 | Lampropoulos et al. ..... 600/485 |
| 5,752,918 A * | | 5/1998 | Fowler et al. ................. 600/488 |
| 5,757,354 A * | | 5/1998 | Kawamura ..................... 345/656 |
| 5,848,971 A * | | 12/1998 | Fowler et al. ................. 600/486 |
| 5,857,777 A * | | 1/1999 | Schuh ........................... 374/172 |
| 5,868,678 A * | | 2/1999 | Brunner et al. ................ 600/486 |
| 5,876,351 A * | | 3/1999 | Rohde ........................... 600/523 |
| 5,961,451 A * | | 10/1999 | Reber et al. ................... 600/322 |
| 6,006,120 A * | | 12/1999 | Levin ............................. 600/323 |
| 6,117,086 A * | | 9/2000 | Shulze ........................... 600/488 |
| 6,134,969 A * | | 10/2000 | Studer et al. ..................... 73/708 |
| 6,186,959 B1 * | | 2/2001 | Canfield et al. ................ 600/559 |
| 6,447,462 B1 | | 9/2002 | Wallace et al. |
| 6,494,830 B1 * | | 12/2002 | Wessel ........................... 600/300 |
| 6,580,086 B1 * | | 6/2003 | Schulz et al. .................. 250/557 |
| 6,580,948 B2 * | | 6/2003 | Haupert et al. .................. 607/60 |
| 6,634,789 B2 * | | 10/2003 | Babkes .......................... 374/208 |
| 6,635,020 B2 * | | 10/2003 | Tripp et al. .................... 600/488 |
| 6,699,188 B2 * | | 3/2004 | Wessel ........................... 600/300 |
| 6,790,178 B1 * | | 9/2004 | Mault et al. ................... 600/300 |
| 6,957,911 B2 * | | 10/2005 | Wong et al. ................... 374/208 |
| 7,021,824 B2 * | | 4/2006 | Wawro et al. ................. 374/208 |
| 7,286,894 B1 * | | 10/2007 | Grant et al. .................... 700/168 |
| 7,373,825 B2 * | | 5/2008 | Fennington, Jr. ................ 73/700 |
| 7,635,354 B2 * | | 12/2009 | Navarro et al. ................ 604/174 |
| 7,747,301 B2 * | | 6/2010 | Cheng et al. .................. 600/322 |
| 2002/0007198 A1 * | | 1/2002 | Haupert et al. .................. 607/30 |
| 2002/0045851 A1 | | 4/2002 | Suzuki et al. |
| 2002/0120200 A1 | | 8/2002 | Brockway et al. |
| 2002/0138017 A1 | | 9/2002 | Bui et al. |
| 2002/0165735 A1 | | 11/2002 | Stangel |
| 2003/0002562 A1 * | | 1/2003 | Yerlikaya et al. ............. 374/208 |
| 2003/0139677 A1 * | | 7/2003 | Fonseca et al. ................ 600/508 |
| 2003/0212379 A1 | | 11/2003 | Bylund et al. |
| 2003/0220607 A1 | | 11/2003 | Busby et al. |
| 2003/0220609 A1 | | 11/2003 | Childers et al. |
| 2004/0059212 A1 * | | 3/2004 | Abreu ............................ 600/373 |
| 2004/0264546 A1 * | | 12/2004 | Wong et al. ................... 374/209 |
| 2005/0049501 A1 * | | 3/2005 | Conero et al. ................. 600/449 |
| 2005/0249263 A1 * | | 11/2005 | Yerlikaya et al. ............. 374/209 |
| 2007/0055227 A1 * | | 3/2007 | Khalaj et al. ..................... 606/41 |
| 2007/0179400 A1 * | | 8/2007 | Dijkman ........................ 600/561 |
| 2007/0189358 A1 * | | 8/2007 | Lane et al. .................... 374/121 |
| 2008/0214939 A1 * | | 9/2008 | Harhen .......................... 600/462 |
| 2009/0069714 A1 | | 3/2009 | Eichmann et al. |
| 2009/0205195 A1 * | | 8/2009 | Yerlikaya ..................... 29/602.1 |
| 2010/0036214 A1 * | | 2/2010 | Rieth ............................. 600/301 |
| 2010/0217101 A1 * | | 8/2010 | Rieth ............................. 600/301 |

FOREIGN PATENT DOCUMENTS

| | | |
|---|---|---|
| EP | 091982 A1 | 11/1998 |
| WO | WO96/14813 A1 | 5/1996 |
| WO | W001/17425 A2 | 3/2001 |
| WO | W002/07595 A1 | 1/2002 |
| WO | W002/22006 A1 | 3/2002 |
| WO | W002/22010 A1 | 3/2002 |
| WO | W003/071944 A1 | 9/2003 |

* cited by examiner

APPARATUS FOR MEDICAL MEASUREMENT

This patent application is a continuation of U.S. patent application Ser. No. 10/572,031, which was the National Stage of International Application No. PCT/NL2003/000635, filed Sep. 12, 2003; and this patent application is a continuation-in-part of U.S. patent application Ser. No. 10/521,340, which was the National Stage of International Application No. PCT/NL2003/000508, filed Jul. 10, 2003, which claimed the benefit of Netherlands Patent Application No. 1021054, filed Jul. 12, 2002.

TECHNICAL FIELD

The invention relates to a measuring device for medical application comprising a first part provided with measuring means for measuring data of a patient, and a second part provided with communication means for sending the data, wherein the first part can be releasably connected to the second part.

BACKGROUND OF THE INVENTION

Known from international patent application publication number WO 02/07595 is a connector unit for receiving a disposable catheter for performing for example urological measurements. In the catheter is arranged a pressure sensor for measuring diverse pressure-related data. The connector unit can be connected by means of electrical wiring to peripheral equipment for the purpose of sending the data thereto.

SUMMARY OF THE INVENTION

It is a general object of the invention to provide a universal measuring device for medical application with an increased number of possible uses.

A further object of the invention is to provide a measuring device which can easily be sterilized prior to use.

A further object of the invention is to provide a measuring device which is safe in use and dedicated to the intended use.

A still further object of the invention is to provide a measuring device having disposable and reusable parts.

Furthermore the present invention aims to provide a method for obtaining data from a human or animal, especially a bodily cavity and a method for manufacturing a device for medical application, according to the present invention.

A number of these and still further objects are obtained with a device or method according to the present invention.

With a device according to the present invention a suitable combination of a first part having measuring means such as a sensor and a second part for transmitting said data can be made, depending on the desired use. The second part is preferably a reusable part comprising for example electronics dedicated to a specific user such as a doctor, hospital or patient, whereas the first part is preferably a disposable part, dedicated for an intended use, such as catheters for pressure measurement in one or more bodily cavities or electrodes for EMG or EEG or the like.

In a preferred embodiment the communication means are wireless communication means such as Bluetooth, increasing the usability of the device. The possible uses are considerably increased through the application of wireless communication, because of the fact, among others, that the patient and the peripheral equipment do not have to be located in the same space. In addition, the measuring device according to the invention is extremely easy to use, which increases user convenience to a significant extent. The absence of wires moreover increases the freedom of movement of the patient to a significant degree.

In a preferred embodiment the first part encloses the second part during use, such that the second part is fully surrounded by the first part. In such embodiment the first part functions as a shield for the second part. The first part can be sterilized in a suitable manner, whereas the second part can be introduced into the housing and does not have to be sterilized. A first part can be unwrapped form a package sterilized after which the second part can be introduced into the first part, preparing the device for use. To this end preferably closing means are provided in the first part for introducing the second part into the first part.

The measuring means can be one or more pressure sensors, provided in or on a catheter in a suitable manner. The pressure sensors are connected to the second part when the second part has been positioned into the first part, such that data obtained with each sensor can be transferred by the communication means.

In a further preferred embodiment the first part is provided with an electronic circuit for control of the first and/or second part. The electronic circuit is preferably provided in a chip.

In a first embodiment the electronic circuit is designed comprising a counter for timing a period after introduction of the second part into the first part, during which period the device is in an operational state, wherein the circuit is designed to bring the device out of the operational state after the period or upon removal of the second part from the first part. This means that the first part can only be used a limited number of times, especially once and/or only during the period or obtaining of the data can be started only during the period. This prevents reuse or improper use of a first part, especially for example catheters attached thereto.

In a second embodiment the circuit is designed for comprising information about at least data to be measured and/or measuring apparatuses attached to the first part, such as catheters with pressure sensing means and/or the second part to be inserted into the first part. The circuit comprises to that end for example a memory such as a ROM or RAM memory. This also has the advantage that when inserting the second part into the first part, the circuit will communicate with the second part and can automatically set the second part for the specific measurement means.

Preferably the circuit comprises both features as discussed before. The first and second part can be provided with locking means, such that only compatible first and second parts can be combined. This prevents insertion of a second part into a first part which is not compatible with the second part.

In a specific embodiment a device according to the present invention is characterized in that it comprises at least one catheter, connected to a pressure chamber on or in the first part, a pressure sensor being provided within or connected to the pressure chamber. During use pressure in a fluid within said pressure chamber can be measured with said pressure sensor, resulting in data to be communicated by the communication means.

Preferably said pressure chamber is provided with at least one pressure relieve opening, provided with a one-way valve, positioned such that fluid can be introduced past the valve into the pressure chamber but not in the opposite direction, wherein prior to use of the device the pressure relief valve is brought into an opened state such that the pressure chamber is in free communication with the environment of the device. The second part and/or the first part are more preferably provided with an electronic circuit for resetting the at least one pressure sensor when said pressure relief valve is in said opened state. This obviates the need of a multi-directional tap or valve. Before use the device can be sterilized with the one way valve in the opened state, having an open communication through the pressure chamber and into the catheter. Upon introduction of the second part into the first part each pressure sensor can be reset. Reset has to be understood as encompassing setting a zero value with reference to the environmental pressure. After setting the one or more sensors, each one way valve is brought back into an operational position, out of the opened state, such that pressure fluid can not flow from the catheter or pressure chamber to the environment past the valve. In a suitable solution a plug can be used to bring and keep temporarily the valve in the opened state, which can be removed after the setting of the at least one sensor. The setting can be done electronically by a suitable circuit in the first and/or second part.

First and second parts as such are also part of the present invention.

The invention further relates to a method for measuring pressure in a bodily cavity using at least one catheter having a sensor, comprising the steps of sterilizing the at least one catheter, connected to a first part of a measuring device together with the first part, inserting a second part into the first part, such that the second part is fully enclosed within the first part, the second part being provided with communication means for transmitting data received from the at least one sensor to recording and/or analyzing means.

With such method the device can easily be prepared for use, without the necessity of sterilizing the second part as such. Moreover, such device can be made relatively small and light, such that it can be worn by a patient.

Moreover the present invention relates to a set of at least one second part and a series of first parts, compatible with the at least one second part.

The present invention furthermore relates to a method for manufacturing a device according to the present invention.

In elucidation of the invention exemplary embodiments of the present invention will hereafter be described, with reference to the drawings.

DETAILED DESCRIPTION OF THE DRAWINGS

Corresponding components are designated in the figures with the same reference numerals. The embodiments shown are only shown by way of example and should not be considered as limiting the invention.

Figure 1:
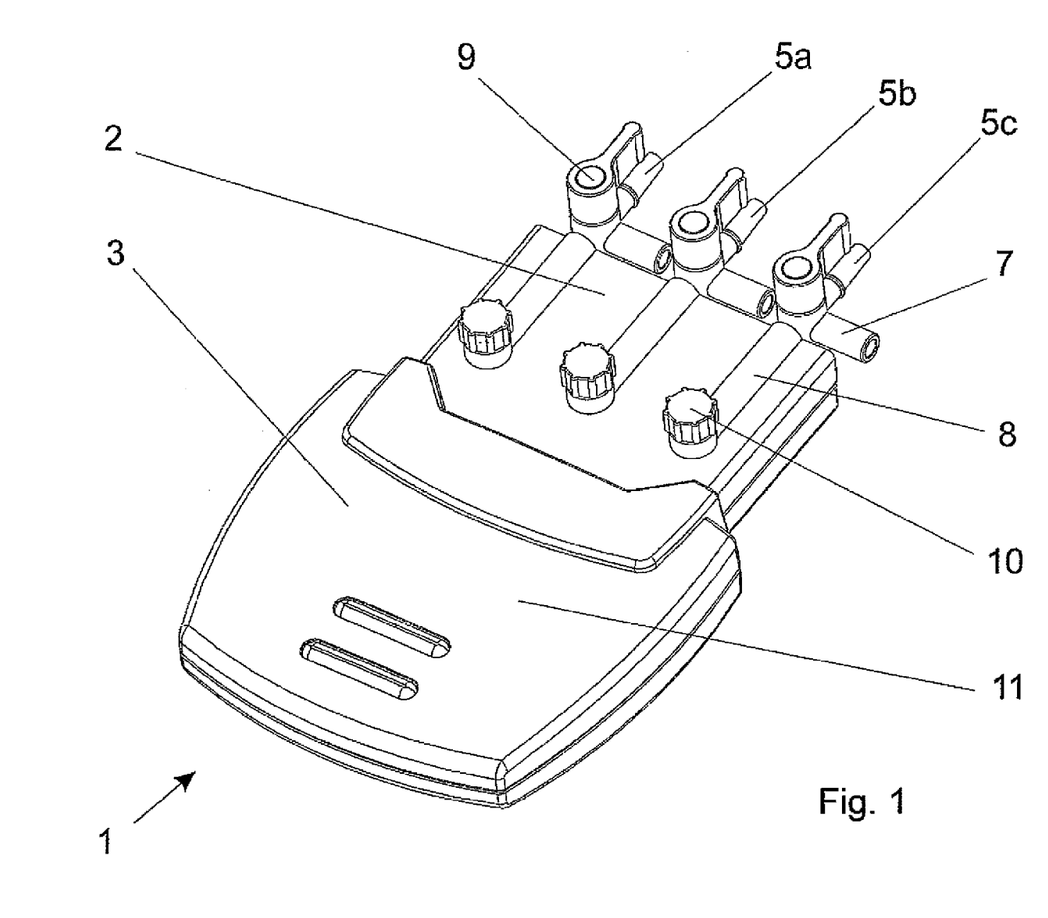
FIG. 1 illustrates in perspective view a first embodiment of the measuring device according to the invention.

FIG. 1 shows a measuring device 1 comprising a cassette 2 forming a first part, which is connected to a cassette holder 3 forming a second part. In this application the reference sign 2 will be used for the first part, in any form (e.g. cassette or housing), the reference sign 3 for the second part, in any form (e.g. holder or module). Cassette 2 is provided with measuring means, which in this preferred embodiment are adapted to perform liquid pressure measurements in the field of urology. The measuring means comprises three catheters 4 which are each provided with three ports, i.e. a first port 5a, 5b, 5c for connection of a catheter tube 6a, 6b, 6c (see FIG. 3), a second venting port 7 and a third port 8 in which is arranged a pressure sensor 20 (not shown). The catheters are further provided with a two-way tap 9 and a non-return valve 10. Such a catheter is described at length in the above stated international patent application publication no. WO 02/07595 which is incorporated herein by reference, at least for the catheters.

It is noted in this respect that the catheters 4 are preferably at least partly integrated into the cassette. The cassette is provided with recesses on which a close-fitting casing is placed in liquid-tight manner, the recesses and casing together forming said part of the catheters 4, especially pressure chambers 18. The components of the catheters and the function thereof correspond however to that of the known catheters, to which reference has been made above.

Figure 2:
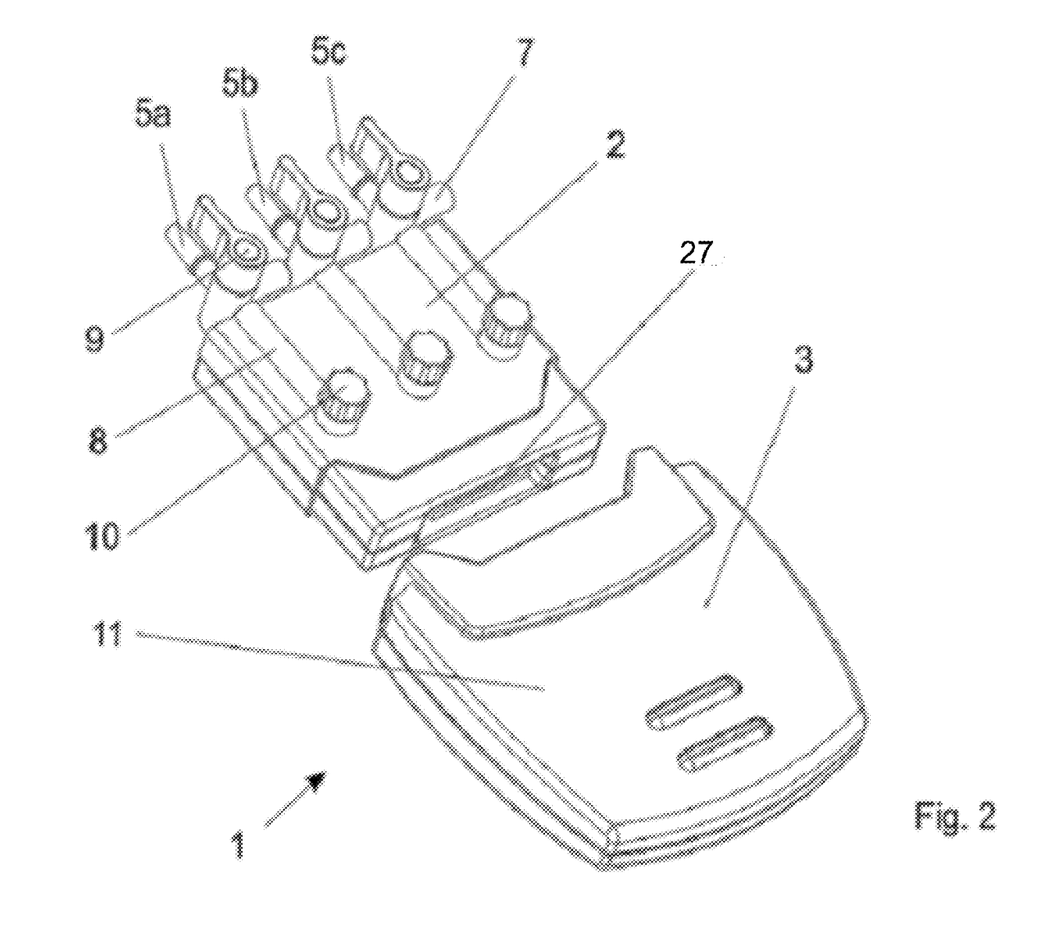
FIG. 2 illustrates the embodiment of FIG. 1 with the parts taken apart.

Cassette 2 can be connected releasably to holder 3 by means of a connector 27, this being illustrated in FIG. 2. It is noted that many types of suitable connectors are available commercially for releasable connection of the cassette 2 and the holder 3.

During use the cassette 2 may come into contact with bodily fluids of the patient and is intended as a disposable article. The holder 3 is preferably provided with a power supply, for instance in the form of batteries. Preferably a rechargeable battery is used such as known from mobile phones. Such battery is robust and light as well as compact. In the cassette 2 a chip 13 is provided, connected to the cassette holder 3 and to the battery, which chip 13 comprises an electronic circuit with a counter or timer. Once the cassette 2 is connected to the holder 3 the counter is initiated and starts timing a preset period of time during which the device can be used, for example for receiving and transmitting data obtained with the pressure sensors. After passing the preset period the chip 13 will stop the device 1 and prevent reuse of the cassette 2. Preferably the chip 13 is designed to allow only one use of the cassette, whereas disconnecting the cassette 2 form the holder 3 will prevent a second use, although disconnecting and reconnecting within the period may be allowable, depending on the setting of the chip 13.

Moreover the chip 13 can be provided with memory means in which data can be stored concerning for example an intended user such as a doctor or hospital, the type of catheters connected to the cassette 2, the intended use and the like. When connecting the cassette 2 to the holder 3 the chip 13 is read by the holder 3, that is by electronics inside the holder 3. A verification cycle is performed and if the data stored in the memory is acknowledged as compatible with the holder 3, the desired data can be obtained with the sensors 20. Otherwise the device will be blocked. This prevents unallowed or improper use. Preferably the chip 13 can be charged with information only once.

Holder 3 is provided with wireless communication means. The communication means comprise at least one transmitter, for instance a radio frequency transmitter 11. All peripherals with a suitable receiver can receive and/or process the data sent by the holder. Examples of such peripherals are computers, such as personal computers, including laptops, as well as electronic agendas, the so-called palmtop. If desired, the communication means can also comprise a receiver, preferably a radio frequency receiver. Suitable wireless communication means are per se known and available commercially. Use is preferably made of a protocol for monitoring the completeness and/or reliability of the received data. Such protocols are per se known and available commercially in the form of software and/or hardware. An example of suitable wireless communication means is the Bluetooth system of IBM.

Holder 3 is further provided with electronics for reading the measurement values of the pressure sensor and converting thereof into data suitable for transmission. Holder 3 comprises for this purpose means for digitizing the data. The holder can also comprise a pre-amplifier. Such electronics are commercially available and therefore known to a skilled person in the field.

Holder 3 is also provided with means for attaching the holder to a patient, such as adhesive electrodes (not shown), and is suitable for stationary and ambulatory use. Holder 3 is suitable and intended for reuse. It can be cleaned simply in the usual manner, for instance with a wet cloth. The holder can be made splashproof by liquid-tight sealing of the connector for the cassette.

Figure 3:
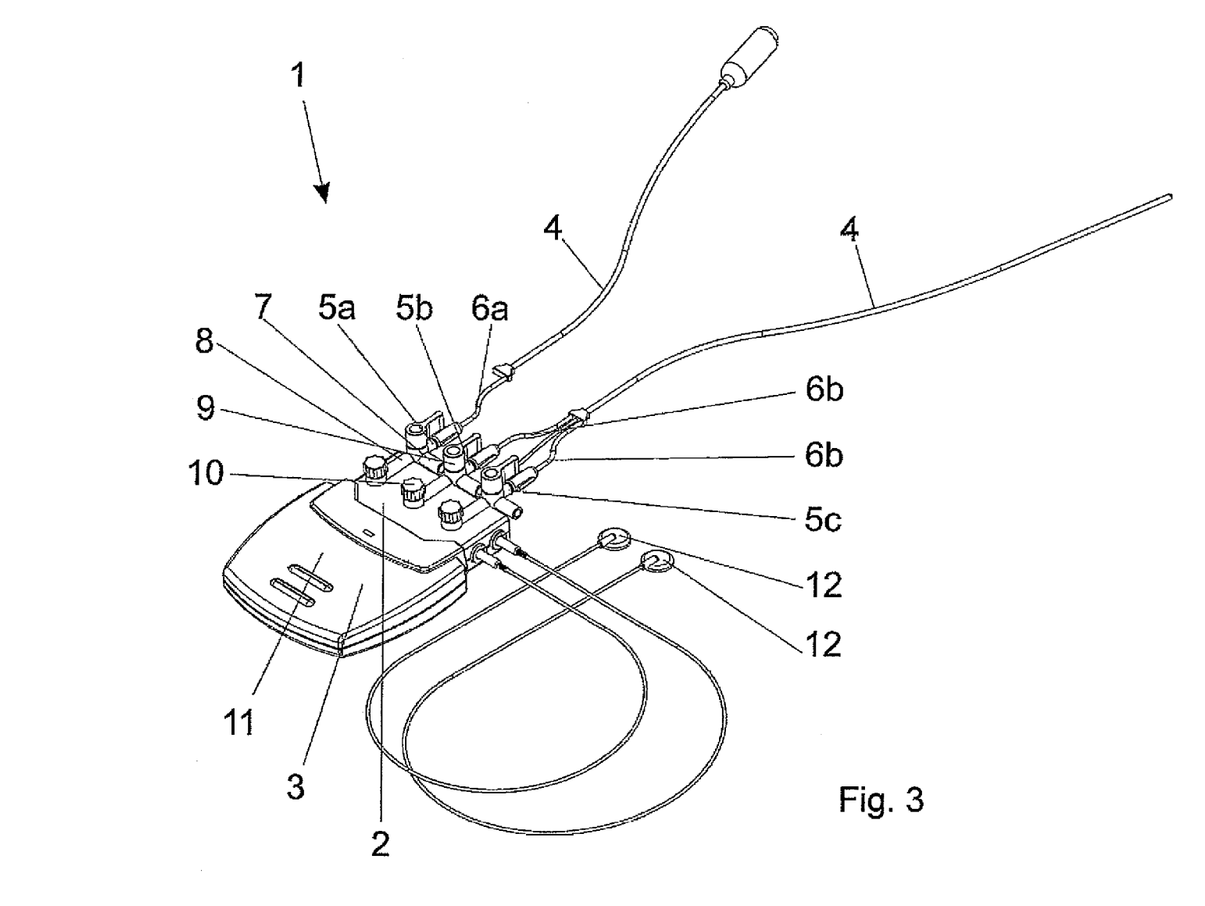
FIG. 3 illustrates the embodiment of FIG. 1 with connections in a practical situation.

FIG. 3 shows measuring device 1 in a practical situation. A catheter tube 6a for rectal measurement of the abdominal pressure is connected to port 5a. A catheter tube 6b for simultaneously measuring the pressure in the urethra and in the bladder is connected to ports 5b and 5c.

Figures 4, 5:
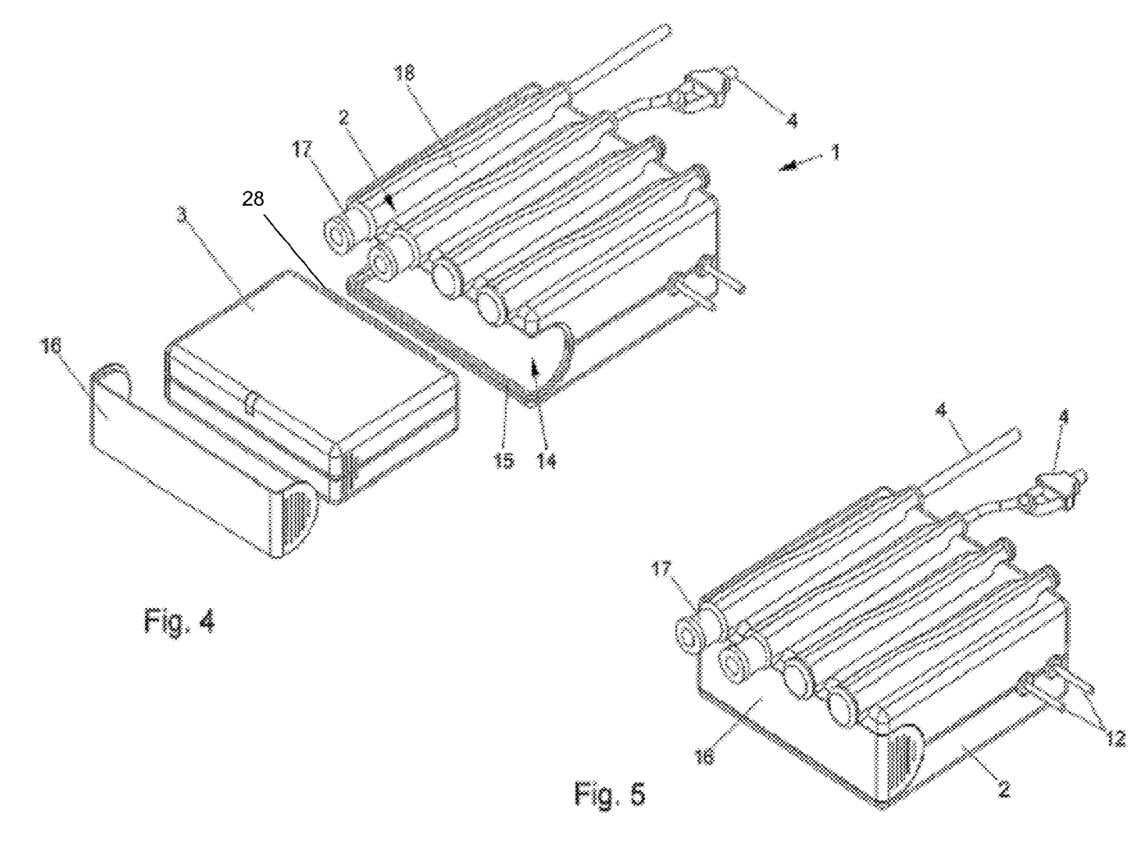
FIG. 4 illustrates a second embodiment of a measuring device according to the present invention, in which a second part can be inserted into a first part, in disassembled position.
FIG. 5 illustrates the device according to FIG. 4, in assembled position.

In FIG. 4, a second embodiment of a device 1 according to the present invention is shown, comprising a first part 2 or cassette, designed as a housing, and a second part 3 or send module. The second part 3 can be inserted into a cavity 14 in the first part 2, through an opening 15 (FIG. 4), which can be closed off by a lid 16 for fully enclosing the second part 3 within the first part 2, shielding the second part 3 from the environment (FIG. 5). This means that the second part does not have to be sterile, whereas the first part 2 can be sterilized without the second part 3 containing the communication means.

As discussed before, the catheters can be connected to or form part of the first part. In the embodiments shown in FIGS. 4-11, the tap as shown in FIGS. 1-3 is removed. A one way valve 17 is inserted into the pressure chamber 18, as will be discussed hereafter, opposite the catheter 4, such that in normal operating condition no fluid can pass the valve 17 from the catheter and/or the pressure chamber 18 to the environment. However, air can pass the valve in the opposite direction if necessary. During sterilizing of the first part 2, especially the catheters and pressure chambers and/or setting of the sensors, the valve may be opened mechanically for providing a free passage along the valve. After setting of the sensors the valve may be closed, for example by removing a blocking means such as a plug. Thus a very simple and economical device is obtained. Setting can be performed automatically upon introduction of the second part into the first part.

The first part is provided with four pressure chambers 18, to each of which a catheter 4 can be attached. Each pressure chambers comprises an opening 19 into the cavity, in or under which opening a pressure sensor 20 can be attached, such that it can measure pressure within the pressure chamber, at least in fluid therein.

Figures 6, 7, 8:
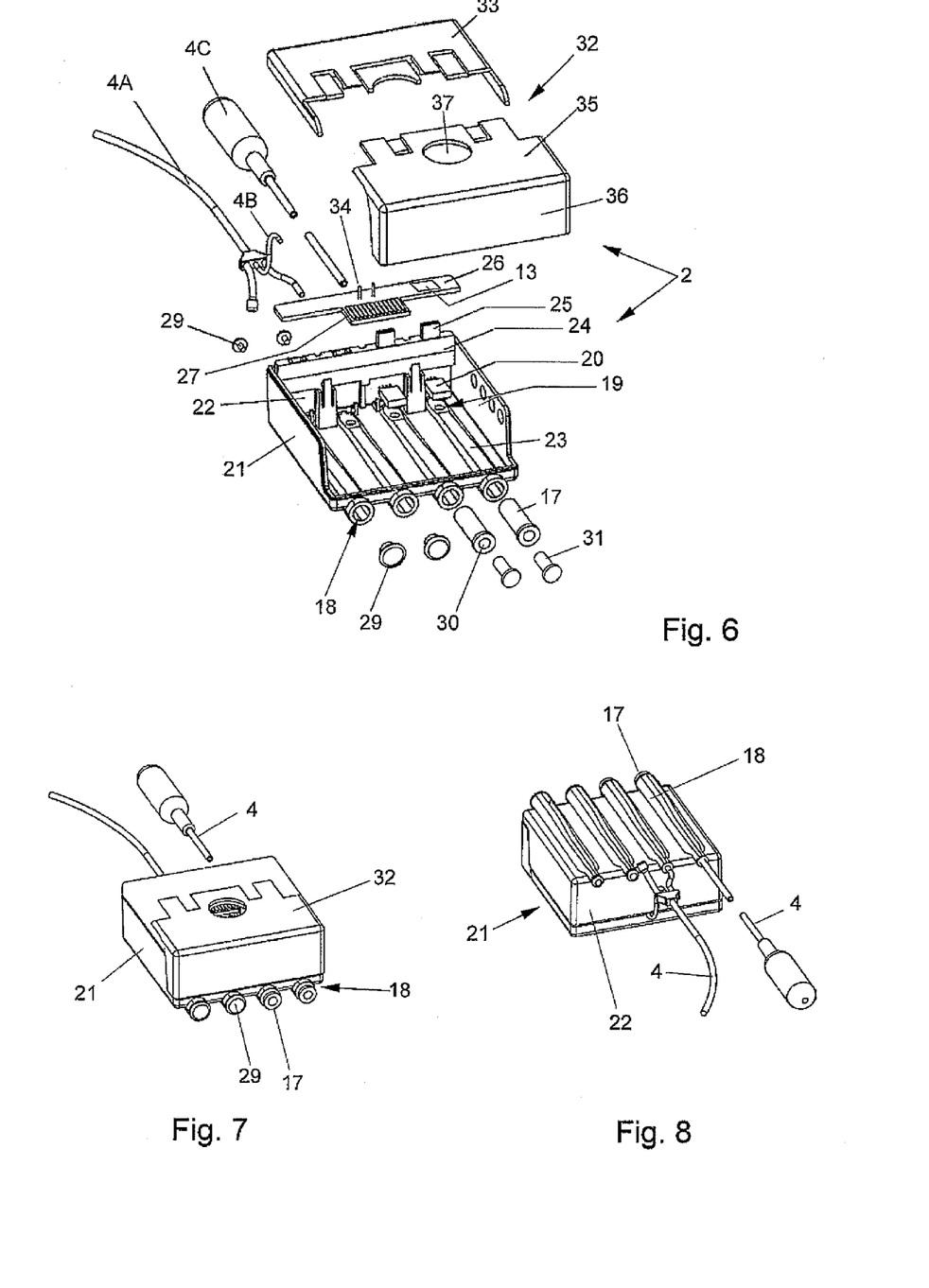
FIG. 6 illustrates a third embodiment of a device, especially of a first part thereof, according to the present invention, in exploded view.
FIG. 7 illustrates a device according to FIG. 6 from a bottom front side, in assembled position.
FIG. 8 illustrates a device according to FIGS. 6 and 7, in a top rear view.

FIGS. 6-11 show an embodiment of a first part 2 of a device according to the present invention, in a modified construction. FIG. 6 shows the device in exploded view, from the bottom side, FIGS. 7 and 8 in bottom and top view.

The first part 2 comprises a bottom part 21 comprising the pressure chambers 18. The openings 19 are visible near an end wall 22. The pressure sensors 20 can be attached to the bottom 23 of the bottom part 21, over the openings 19, after which a connecting board is slid against the wall 22, over the pressure sensors 20. Interconnectors 25 are slid into the connector board 24 for each sensor 20. Then a connecting plate 26 is positioned on top of the interconnectors 25, which connecting plate 26 comprises a first connector 27 and the chip 13. Electrical connections (not shown) are provided for connecting interconnectors 25, the chip 13 and the first connector 27.

The second part 3, as shown in FIG. 4, includes a second connector 28 for connecting to the first connector 27, similar to the connectors as discussed with reference to FIGS. 1-3, for exchange of data and other information and power. In the device 1 as shown in FIGS. 6-11, to only two pressure chambers 18 a catheter is connected, for example by gluing. Shown are a triple lumen catheter 4A with leakage detection 4B and a balloon catheter 4C but obviously any kind of catheter can be connected, based on for example the choice of the manufacturer and/or desires of the user. As shown, the triple lumen catheter has an electrical leakage detector that can be attached to the connecting plate by connecting pins 34. In the relevant two pressure chambers 18 connected to a catheter 4, a one way valve 17 is inserted, for example manufactured by Qosina. The other two pressure chambers are closed off on both sides by suitable lids 29. Into the opening 30 of each valve 17 a plug 31 is inserted, such that the valve is brought and held in an opened position, for sterilization and/or setting, as discussed. The plugs 31 can for example be hollow and can be clamped into the openings 30, such that they can easily be removed before measuring data. It should be noted that such plug or similar means could also be used with a catheter according to WO 02/07595.

The first part 2 further comprises a lid 32, for closing the first part 2. The lid 32 comprises two parts, an upper part 33 which can be secured to the bottom part 21 at the side of the end wall 22. A lower part 35 can be slid in and over the upper part 33, having an end wall 36 such that the lid 32 will close off the housing or first part 2 around a second part 3 connected to the connecting plate 26. In the lid 32 an opening 37 can be provided in which a sensor or other attachment means can be provided for connecting the first part 2 to means for wearing the device, for example on an arm, leg, garment or the like, as discussed with respect to the embodiment according to FIGS. 1-3. Once the lid is positioned, the first part 2 is hermetically closed and shields a second part 3 positioned therein from the environment and vice versa.

FIG. 7 shows the assembled device 1 of FIG. 6 from the bottom, while FIG. 8 shows the assembled device 1 of FIG. 6 from the top.

Figure 9:
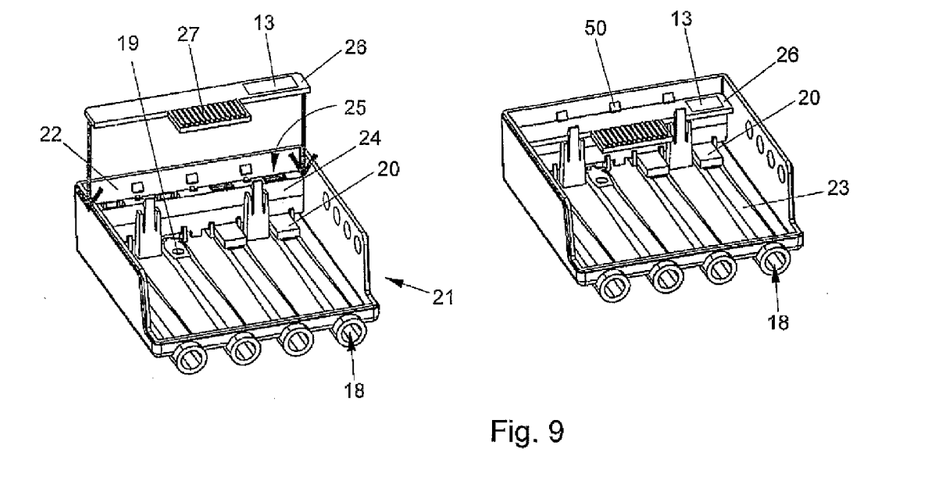
FIGS. 9-11 illustrates a device according to FIGS. 6-8, in various assembling steps.

A device 1 according to FIG. 6 can be made by manufacturing the bottom part 21, for example by injection molding, including the hollow pressure chambers 18, after which the sensors 20 are positioned over the openings 19, for example by gluing. Then the connecting board 23, the interconnectors 24 and the connecting plate are brought into position. Suitable snap means 50 are provided for locking these into position, as shown in FIG. 9.

Figure 11:
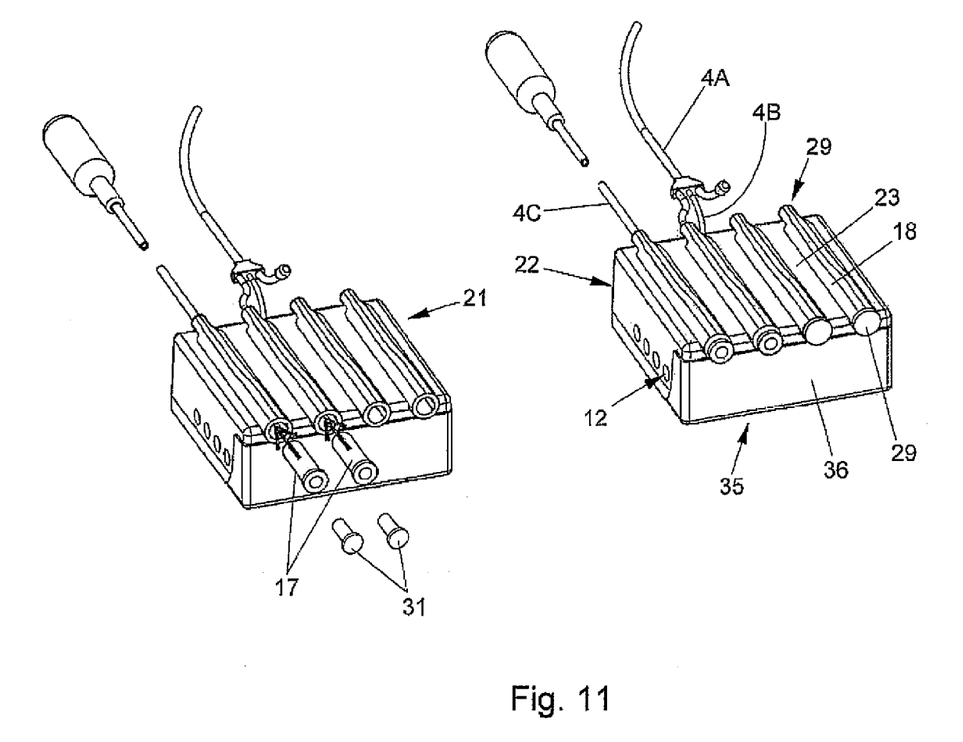

Then the bottom part 21 is sent to for example a manufacturer of catheters, who will prepare the bottom part for a specific customer by attaching the appropriate catheters 4 to the pressure chambers 18, for example by gluing, welding, snap fitting or the like, preferably such that they can not be removed, as is shown in FIG. 11. Then the chip 13 will be programmed with information about for example the catheters 4, the intended use, the intended user or any other information thought appropriate. Obviously this may also be done at the site of manufacturing the device itself.

Figure 10:
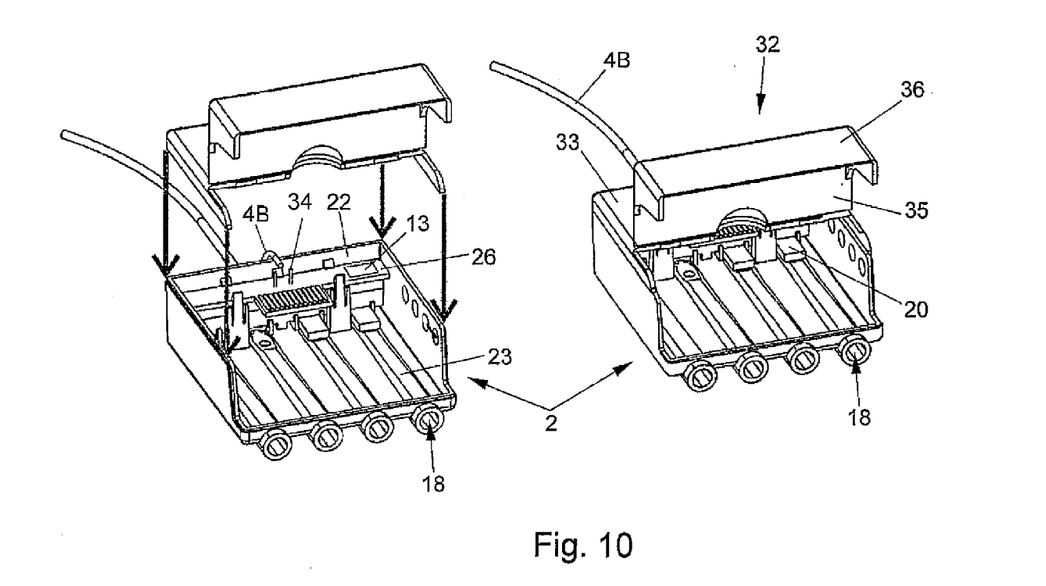

The lid 32 will be placed, as is shown in FIG. 10, together with the valves 17 with plugs 31 and lids 29. The first part 2 comprising the catheters will then normally be sterilized, wrapped in a wrapper and sent to the user ready for use.

The user has a second part 3, dedicated to for example him, his hospital and/or to specific first parts 2. When the device 1 is to be used for example measurement of pressures within one or more cavities, the catheters 4 are appropriately positioned and the lower part 35 is removed or hinged open, after which the second part 3 is slid into the cavity 14 and connected to the first part 2, particularly to the connector 27. The lid 32 is then closed and the device is ready for use.

Upon connecting the second part 3 to the first part 2 the chip 13 and the second part will exchange a recognition protocol. If the first part is recognized and authenticated by the second part, then the device is in an operating state. The sensors will be set automatically to the environmental pressure, due to the open connection between the pressure chamber and the environment, past the one way valve. This pressure will be used as reference pressure. Once the sensors 20 are reset, the plugs 31 are removed, closing the valves 17 and the actual pressures can be measured and the data can be stored and/or transmitted.

As discussed before, upon connecting the connectors 27, 28, a timer is set in the chip 13, timing a period in which the device can be used or during which at least the measurement of data has to commence. Would the second part be removed again within a certain time after said connecting, it may be reloaded but after the time, which is preferably considerably shorter then the period, reconnecting will be useless because the chip 13 will prevent reuse. The first part is a disposable part to be used only once.

A measuring device according to the invention is described in the context of urological applications. It will however be apparent to a skilled person in the field that the measuring means can if desired be replaced by diverse other measuring means for use in other fields of medical science. An example of such measuring means are means for measuring electrophysiological data, for instance measuring electrodes. The measuring device is then suitable for performing a general electrophysiological examination, such as ECG measurements and gastro-enterological measurements. The skilled person will have no difficulty whatever in also using other, per se known measuring means in combination with the above described measuring device.

In FIG. 3, in addition to the catheters, two measuring electrodes 12 are connected to cassette 2 to perform ECG measurements. This is also possible in the embodiments of FIGS. 4-11.

The present invention is by no means limited by or to the embodiments as shown or discussed. Many variations are possible within the frame as set by the claims. For example combinations of parts of the embodiments can be made, another number of catheters can be used and these can be connected in a different manner. Other means may be provided for timing the period, which may be set off in a different manner, for example by closing the lid 32 or by first receipt of data from the sensors.

The second part and the first part may be provided with cooperating locking means, allowing only a second part with a first locking means, for example a pin, to be used with a fitting second locking means, for example a hole. This is a further obstacle to inappropriate use of a wrong first or second part. A first part according to the present invention may be manufactured without a chip and may be suitable for multiple use. Other communication means may be used, even wired communication, although wireless is preferred.

The invention claimed is:

1. A cassette comprising:
   a housing including
      a bottom part, and
      a lid,
      said bottom part and said lid form an enclosure;
   at least one probe connector connected to said housing;
   for at least one of said at least one probe connector, at least one sensor in communication with said respective probe connector;
   a connector in communication with said at least one sensor; and
   a circuit located in said enclosure and in electrical communication between said at least one sensor and said connector, said circuit includes a timing circuit having a counter that prevents transmission of monitoring data being sent through said connector after a predetermined time has passed after connection to a communications module.

2. The cassette according to claim 1, wherein said circuit includes electrical components for controlling operation of said at least one sensor.

3. The cassette according to claim 1, wherein at least one of said at least one probe connector includes
   a catheter connector,
   a pressure chamber, and
   said catheter connector and said pressure chamber together have a passageway running from said catheter connector into said pressure chamber.

4. The cassette according to claim 3, wherein said sensor connected to said pressure chamber includes a fluid pressure sensor.

5. The cassette according to claim 3, wherein said pressure chamber includes at least one pressure relief opening having a one-way valve positioned such that fluid can be introduced past said valve into said pressure chamber,
   wherein when the pressure relief valve is brought into an opened state the pressure chamber is in free communication with an environment around said cassette.

6. The cassette according to claim 3, further comprising at least one catheter connected to said at least one catheter connector.

7. The cassette according to claim 3, further comprising at least one one way valve where said one way valve is connected to a pressure chamber.

8. The cassette according to claim 3, further comprising a cover over at least one pressure chamber.

9. The cassette according to claim 1, further comprising at least two electrode connectors on an outside of said housing, said electrode connectors electrically connected to said connector.

10. The cassette according to claim 1, further comprising a plate, said connector extending from said plate, said plate having at least one connecting pin configured to be attached to at least one module.

11. A cassette comprising:
    a housing including
       a bottom part, and
       a lid having a upper part and a lower part in interlocking fit such that said lower part is pivotable about said upper part to provide access to an area enclosed by said bottom part and said lid,
       said bottom part and said lid form an enclosure;

at least one probe connector connected to said housing;

for at least one of said at least one probe connector, at least one sensor in communication with said respective probe connector;

a connector in communication with said at least one sensor, said connector located in the enclosure formed by said bottom part and said lid; and a circuit located in said enclosure and in electrical communication between said at least one sensor and said connector.

12. A module comprising:

a housing;

a connector member connected to said housing and accessible externally to said housing, said connector member configured to releasably connect to a cassette having at least one sensor;

a wireless transmitter connected to said connector member, said transmitter is located substantially in said housing;

a power supply connected to said transmitter and said connector member, said power supply located inside said housing;

means for processing information received through said connector member, means for transmitting control signals through said connector member, and means for transmitting information through said transmitter.

13. The system according to claim 12, wherein said module includes means for verifying that a cassette attached to said module is compatible to operate with said module, said verifying means will prevent operation of the cassette when a verification fails; and means for reading values produced by said at least one sensor in said cassette during operation of the system.

14. A system comprising:

a cassette having a cassette housing;

at least one probe connector connected to said cassette housing;

for at least one of said at least one probe connector, at least one sensor in communication with said respective probe connector; and a connector in communication with said at least one sensor, and a module having a module housing;

a connector member connected to said module housing and accessible externally to said module housing by said connector of said cassette, when said connector and said connector member are connected, an electrical connection is established between said cassette and said module; and a transmitter connected to said connector member.

15. The system according to claim 14, wherein said cassette further comprising a circuit located in said cassette housing and in electrical communication between said at least one sensor and said connector such that an electrical pathway is formed from said at least one sensor to said circuit to said connector.

16. The system according to claim 15, wherein said circuit includes electrical components for controlling the operation of said at least one sensor.

17. The system according to claim 15, wherein said circuit includes a timing circuit having a counter that prevents transmission of monitoring data being sent through said connector after a predetermined time has passed after said cassette is connected to said module.

18. The system according to claim 14, wherein said module further includes means for processing information received from said at least one sensor through said connector member and said connector, means for transmitting control signals to said at least one sensor through said connector member and said connector, and means for transmitting information through said transmitter.

19. The system according to claim 14, wherein said module includes means for verifying that a cassette attached to said module is compatible to operate with said module, said verifying means will prevent operation of the cassette when a verification fails; and means for reading values produced by said at least one sensor in said cassette during operation of the system.

20. The system according to claim 14, wherein said module fits and is substantially enclosed within said cassette housing during use of said system.

21. The system according to claim 14, wherein said cassette includes a hole passing through one side of said cassette housing, and said module including a sensor connector that is aligned with the hole of said cassette housing when said module is enclosed in said cassette housing.

* * * * *